US00PP32110P2

(12) United States Plant Patent
Hancock

(10) Patent No.: US PP32,110 P2
(45) Date of Patent: Aug. 25, 2020

(54) BLUEBERRY PLANT DENOMINATED 'KATAHDIN'

(50) Latin Name: *Vaccinium corymbosum*
Varietal Denomination: Katahdin

(71) Applicant: Board of Trustees of Michigan State University, East Lansing, MI (US)

(72) Inventor: James F. Hancock, East Lansing, MI (US)

(73) Assignee: Board of Trustess of Michigan State University, East Lansing, MI (US)

( * ) Notice: Subject to any disclaimer, the term of this patent is extended or adjusted under 35 U.S.C. 154(b) by 0 days.

(21) Appl. No.: 16/501,634

(22) Filed: May 14, 2019

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./157
CPC ..... A01H 5/08; A01H 6/36
See application file for complete search history.

(56) References Cited

U.S. PATENT DOCUMENTS

PP15,103 P3 8/2004 Hancock
PP26,031 P3 11/2015 Hancock

*Primary Examiner* — Annette H Para
(74) *Attorney, Agent, or Firm* — McKee, Voorhees & Sease, PLC

(57) ABSTRACT

Katandin is a new blueberry variety of *Vaccinium corymbosum* from the Michigan State University breeding program. Is comprised of primarily *Vaccinium corymbosum*, with about 7% of its genes coming from *V. darrowii*, 4% from *V. angustifolium* and <1% from *V. tenellum* and *V. ashei*. It is a highly productive cultivar with excellent fresh fruit quality. It is well adapted to all northern highbush production areas. Canes are numerous, moderately branched and the fruit are well exposed. Its berries are large, have small, dry picking scars, medium blue color, good firmness and flavor. Katandin is characterized by high yields, high vigor and strong winter hardiness.

4 Drawing Sheets

Botanical designation: The present invention relates to a new Northern Highbush blueberry variety.

Latin name and variety denomination: The present invention relates to a new and distinct variety of *Vaccinium corymbosum*, which is hereby denominated "Katandin."

SUMMARY OF THE INVENTION

This invention relates to a new and distinct variety of highbush blueberry plant. It has as its maternal parent MSU 46 and its Paternal parent is Draper. 'Katandin' is primarily *Vaccinium corymbosum*, with about 7% of its genes coming from *V. darrowii,* 4% from *V. angustifolium* and <1% from *V. tenellum* and *V. ashei*. It is a highly productive cultivar with excellent fresh fruit quality. It is likely well adapted to all northern highbush production areas. Plants of 'Katandin' are vigorous and upright, although the canes can be lax when loaded with fruit. Canes are numerous, moderately branched and the fruit are well exposed. Its berries are large, have small, dry picking scars, medium blue color, good firmness and flavor.

The fruiting season of 'Katandin' significantly overlaps that of the widely planted, mid-season cultivars 'Draper', and 'Bluecrop'. 'Katandin' has larger, firmer fruit than 'Bluecrop' and a much smaller picking scar. Its fruit can be a little smaller than 'Draper' but otherwise has comparable fruit quality. It is a much more vigorous than 'Draper' and is more productive.

'Katandin' is meant as an alternative with improved hardiness for cold climates like Michigan. 'Katandin' has high yields, high vigor and strong winter hardiness.

PRIOR VARIETIES

Among the existing varieties of blueberries, which are known to us, and mentioned herein, 'Draper' U.S. Plant Pat. No. 15,103; 'MSU 46' (not patented); 'Bluecrop' (not patented); and 'Osorno' (U.S. Plant Pat. No. 26,031).

ORIGIN OF THE VARIETY

Breeding procedures: Emasculated flowers of 'MSU 46' were pollinated in 2004 with pollen from 'Draper'. MSU 46 is a sister of 'Huron' released from MSU in 2011. The seeds were germinated, grown in a greenhouse for 1 year and then field planted at the Southwest Michigan Research and Extension Center (SWMREC) in Benton Harbor, Mich. MSU 96 was first selected from a group of 121 siblings in 2009 by Jim Hancock (MSU).

ASEXUAL REPRODUCTION OF VARIETY

The original selection of MSU 96 was evaluated at the Southwest Michigan Research and Extension Center at Benton Harbor, Mich. from 2006-2010. Softwood cuttings were also set in advanced trials at Grand Junction, Mich. (MBG Marketing), Silverton, Oreg. (Oregon Blueberry Company), Lowell, Oreg. (Fall Creek Nursery) and Grubbenvorst, Netherlands (Schrijnwerkers Blueberries). Two-year-old plants were planted at 4×10' spacing in Michigan in 2011 and the other locations in 2012. The plantings in Michigan and Oregon were evaluated for three years, and the one in the Netherlands for two years. The plants were evaluated by Jim Hancock and Ed Wheeler (MBG Marketing) in Michigan, Peter Bouches and Dave Brazelton (Fall Creek Nursery), Bob Gabriel (Oregon Blueberry) and Leon Schrijnwerkers (Schrijnwerkers Blueberries).

STATEMENT OF STABILITY

Asexual propagation as described has demonstrated that the combination of traits that characterize this blueberry are fixed and remain true to type through at least two successive propagation cycles.

BRIEF DESCRIPTION OF PHOTOGRAPHS

The present invention will become more fully understood from the detailed description and the accompanying drawings, wherein.

DESCRIPTION OF THE NEW VARIETY

Figure 1:
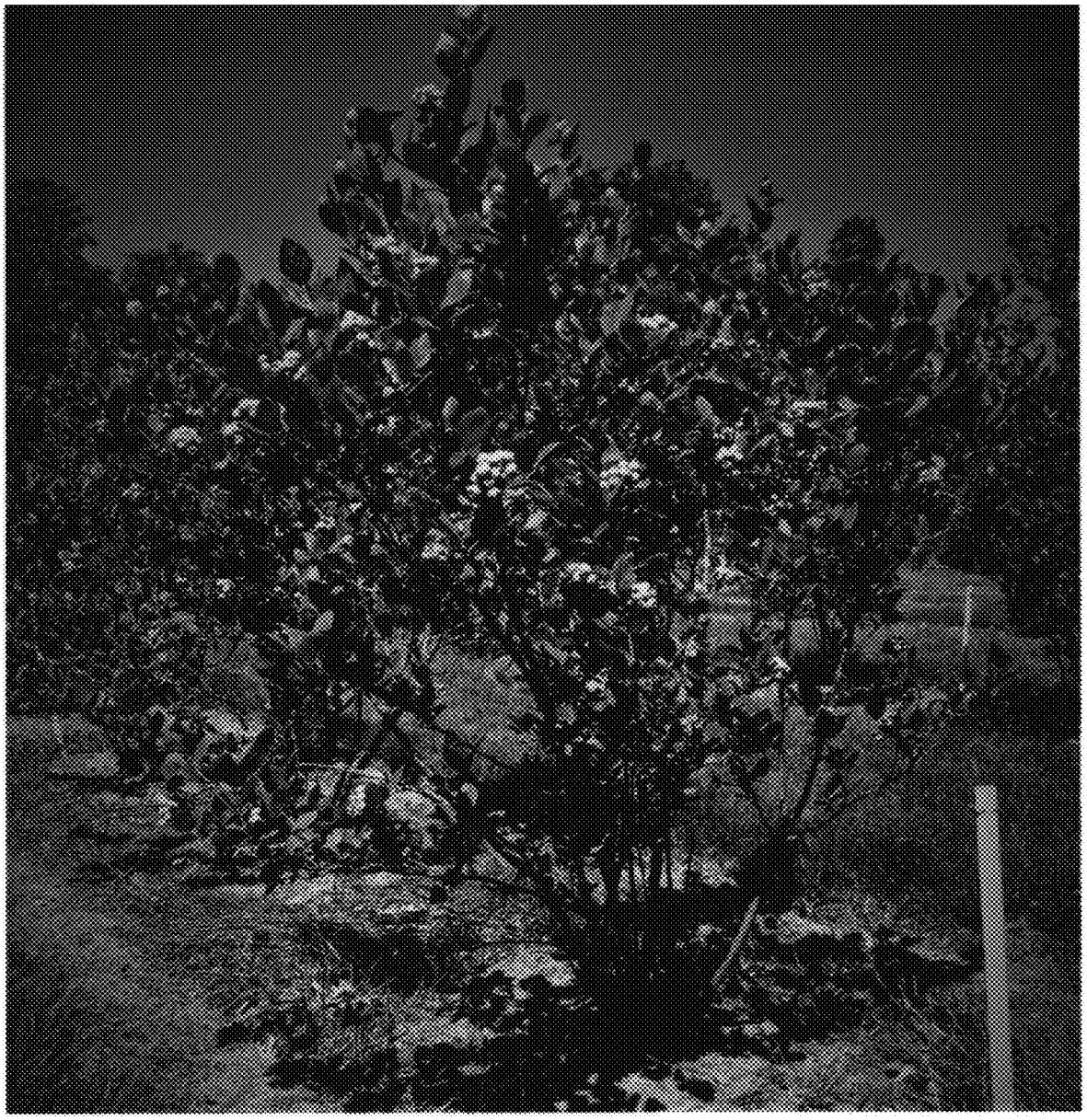
FIG. 1 is a photographic print in full color of a 4-year-old Katandin blueberry plant with green fruit in a planted row in the foreground.
Figure 2:
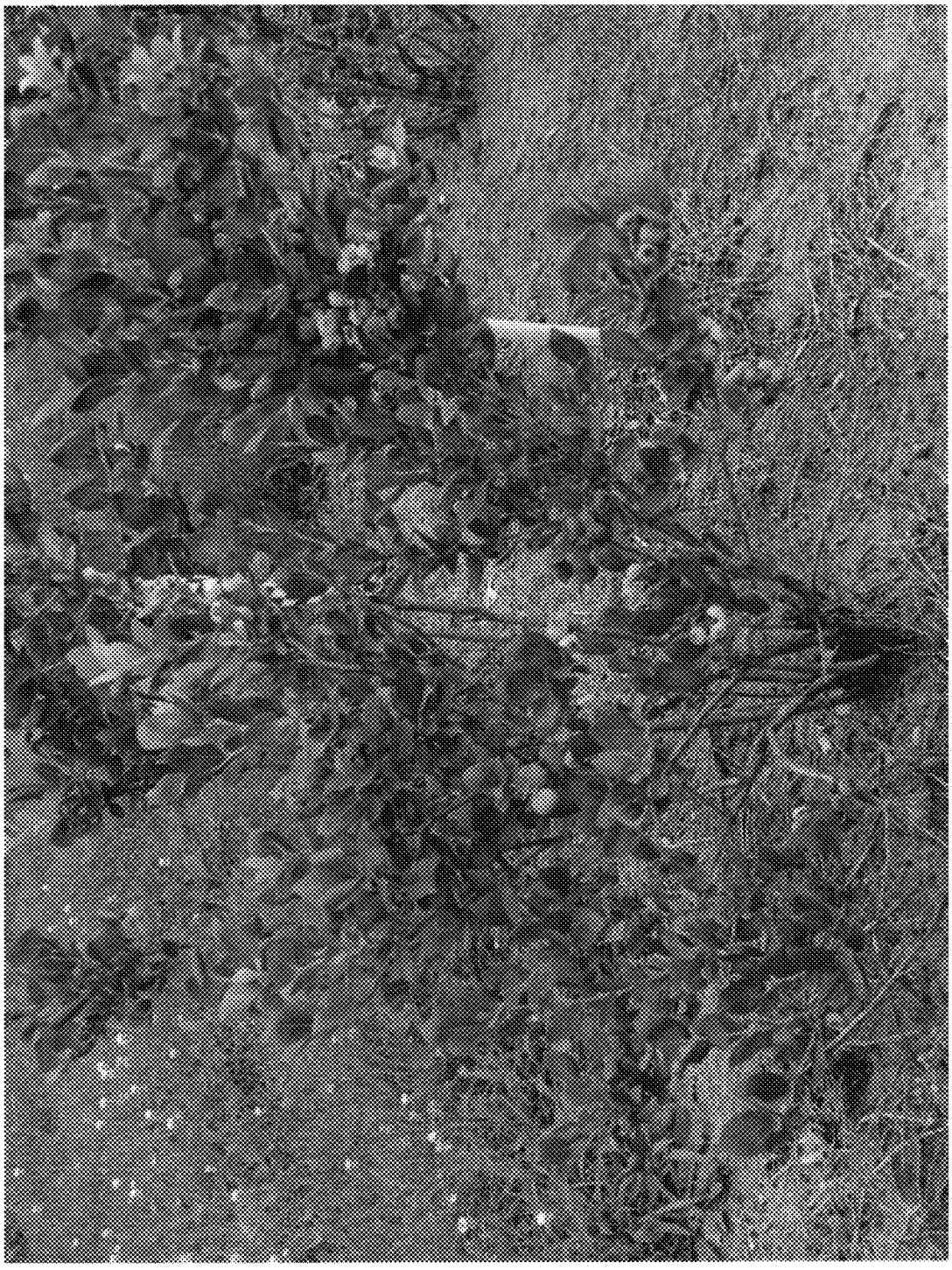
FIG. 2 is a photographic print in full color of a 4-year-old Katandin blueberry plant with blue fruit in a planted row in the foreground.
Figure 3:
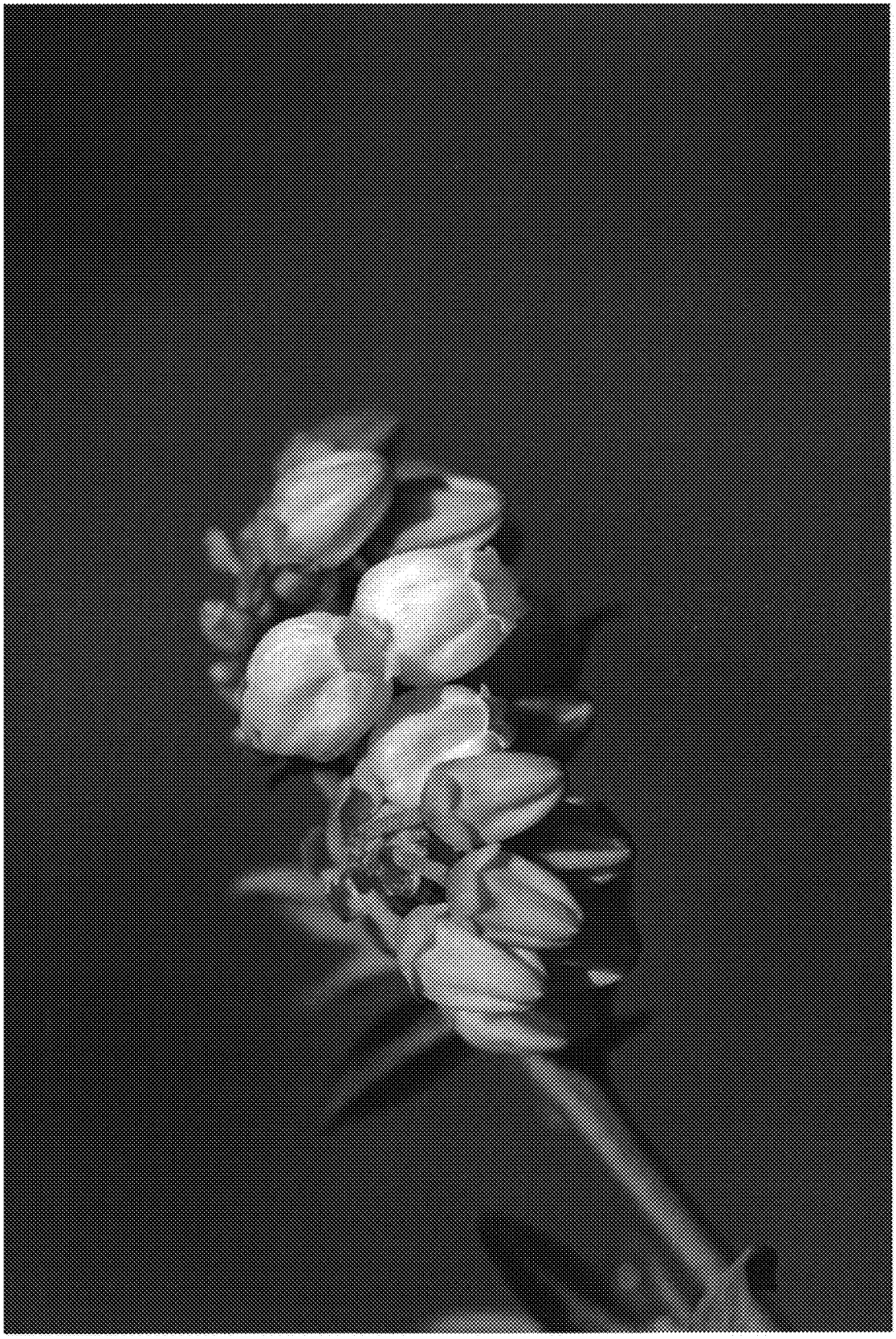
FIG. 3 is a photographic print in full color of a 4-year-old Katandin plant with flowers.
Figure 4:
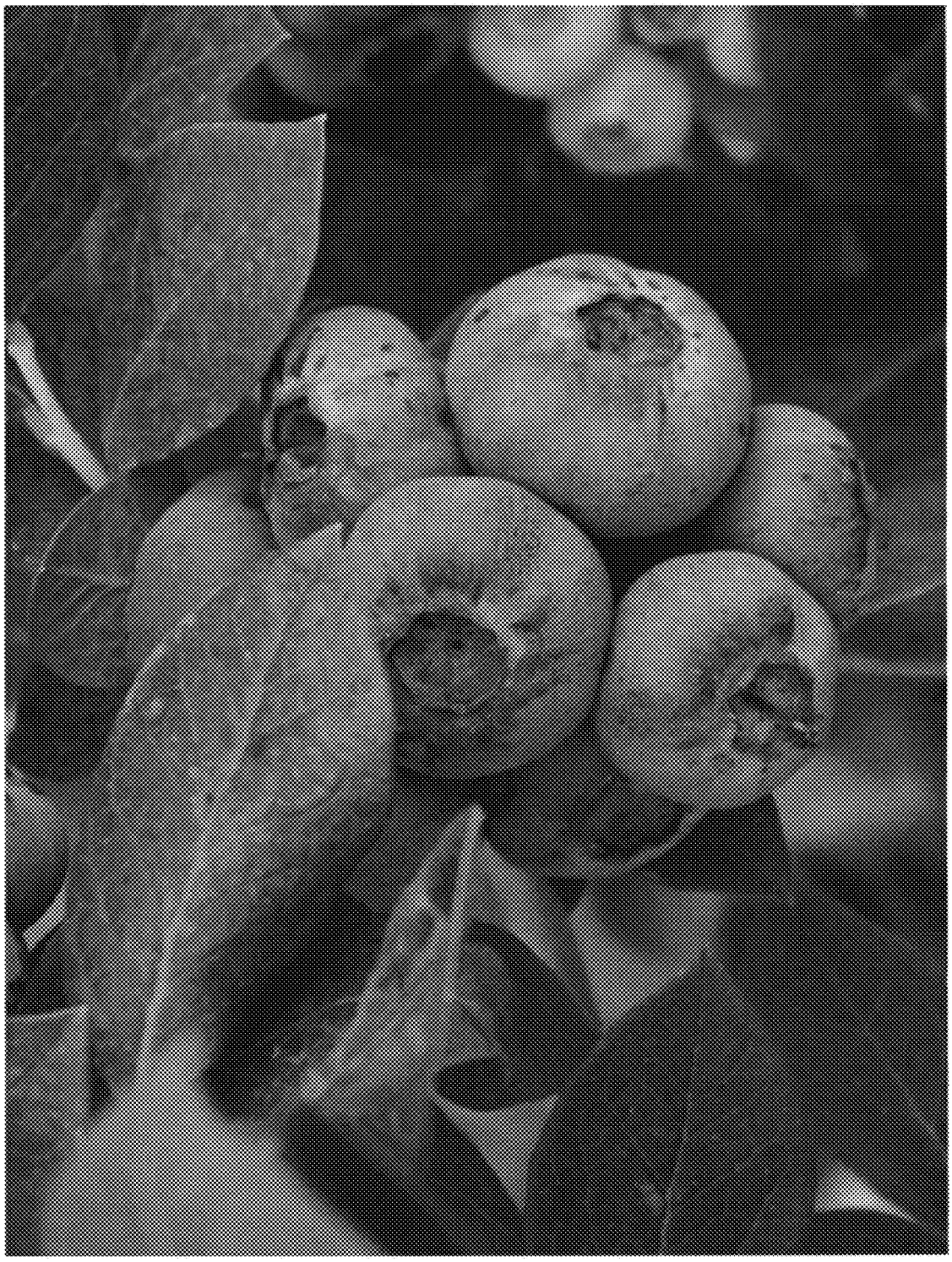
FIG. 4 is a photographic print in full color of fruit clusters of a 4-year-old Katandin blueberry plant. Most, but not all, of the fruit shown is mature.

The following is a detailed botanical description of the new and distinct variety of blueberry, its flowers, fruit and foliage, based on observations of specimens grown at Benton Harbor Mich. and Grand Junction, Mich. over four years, and at South Haven, Mich., Lacota, Mich., Corvallis, Oreg., and Lowell, Oreg., over a two year period. The taxonomic characteristics chosen in the detailed description are standard in the practice (R E Gough, R J Hindle, and V G Shutak, "Identification of Ten Highbush Blueberry Cultivars using Morphological Characteristics," HortScience 11 (5): 5124, 1976). Color descriptions, except those given in common terms, are presented in Royal Horticultural Society Colour Chart designations. In cases where the color descriptions cited from The Royal Horticultural Society Colour Chart differ from the colors shown in the drawings, the colors cited from The Royal Horticultural Society Colour Chart should be considered accurate. Any deviation from these colors in the drawings is due to failure of the photographic process to exactly duplicate the colors of nature. In addition, fruit color designations in Table I are applicable only to mature fruit.

TABLE 1

| 'Katahdin' characteristics | |
|---|---|
| Plant traits | |
| Mature height | 1.40 m |
| Mature width | 1.05 m |

TABLE 1-continued

| 'Katahdin' characteristics | |
|---|---|
| Height/width ratio | 1.33 |
| Growth habit | upright |
| Annual renewal canes | 2-4 |
| Internode length on spring shoots | 1.56 cm average (range 1.4-1.7) |
| Mature cane color | Grayed green, 197 A |
| Mature cane length | 1.07 m (range 80-140) |
| Mature cane width | 3.7 cm (range 26-41) |
| Bark texture | Rough and flakey |
| New shoot color | primarily green |
| Foliage | |
| Leaf shape | obtuse |
| Apex shape | acute |
| Base shape | rounded |
| Leaf length | 5 cm average (range 4.4-5.0 cm) |
| Leaf width | 2.4 cm average (range 2.1-2.8 cm) |
| Leaf length/width ratio | 2.1 |
| Leaf margin | entire |
| Leaf nectaries | absent |
| Pubescence | none |
| Color upper surface | green (137A) |
| Color lower surface | green (138B) |
| Petiole length | 1.7 cm average (range 1-2 cm) |
| Petiole color | light yellowish green (142C) |
| Bud | |
| Bud shape | ovate |
| Bud width | 3.8 mm average (3.0-4.0 mm range) |
| Bud length | 55.2 mm average (5.0-6.0 mm range) |
| Color | reddish brown |
| Blossoms | |
| Shape of corolla | Round-urceolate |
| Calyx | 5 lobed |
| Style length | 8-9 mm |
| Color of open flower | White with pink blushes |
| Flower # per cluster | 8 average (range 5-10) |
| Pistil | one per flower |
| Pistil color | yellowish green (145A) |
| Pistil length | 8-9 mm |
| Flower diameter | 8-9 mm |
| Flower length | 10-11 mm |
| Fragrance | faint blueberry aroma |
| Calyx diameter | 5 mm |
| Sepals | fused, 5 lobes |
| Length | 1-2 mm |
| Width | 1 mm |
| Color top | yellowish green (146C) |
| Color bottom | yellowish green (146C) |
| Reproductive organs | |
| Type | berry |
| Seed size | 1.32 mm |
| Number of seeds | 12.7 average (ranges 5-32) |
| Mature fruit | |
| Height | 1.1 cm average (range 1.0-1.2 cm) |
| Width | 1.6 cm average (range 1.5-1.7 cm) |
| Shape | oblate |
| Color with bloom | violet blue (98D) |
| Color without bloom | violet blue (103A) |
| Pedicel scar size range | 1.5-2.0 mm (1.8 mm average) |
| Pedicel length | 7-8 mm |
| Pedicel color | yellowish green (144B) |
| Peduncle length | 11-13 mm |
| Peduncle color | yellowish green (138A) |
| Average weight | 2.44 g |

PERFORMANCE AND QUALITY DATA

In multi-location trials, 'Katandin' has proven to be an extremely upright very vigorous bush that ripens fruit in the early mid-season (Table 2). Its fruit have had good to excellent size, color, firmness and flavor. It has also annually produced good to excellent yields.

In comparative Michigan trials, 'Katandin' has ripened a few days later than 'Draper' and 'Bluecrop' and before Legacy and Osomo (Table 3). 'Katandin' has a much better plant habit than 'Bluecrop', is more winter hardy and has a much smaller fruit scar. It is a little darker than 'Bluecrop' but otherwise its fruit quality is slightly better or comparable to 'Bluecrop'. 'Katandin' is much more upright and vigorous that Draper, with comparable fruit quality.

The fruit weight of 'Katandin' was among the largest of the varieties sampled in Grand Junction in 2016 and 2017 (Table 4). It had among the firmest berries in 2016 and had similar firmness to all other varieties except 'Duke' in 2017. Its soluble solids were among the highest in both years, while its acidity was on the high but acceptable range in 2017, comparable to 'Draper'.

'Katandin' is intended for all northern highbush production areas including Michigan, the eastern US and Canada, central Chile, Europe, SE Asia, China and the Pacific Northwest.

TABLE 2

Development and fruit characteristics of 'Katahdin' evaluated at one location in Michigan, two in Oregon and one in Denmark.

| | | Fruit characteristics | | | | |
|---|---|---|---|---|---|---|
| Location | | Year | Habit | Season | Vigor | Yield |
| Michigan | Grand Junction | 2014 | 9 | 4 | 7 | 8 |
| | | 2015 | 9 | 2 | 8 | 7 |
| | | 2016 | 9 | 4 | 8 | 7 |
| Oregon | Lowell | 2014 | 9 | 4 | — | 8 |
| | | 2015 | 9 | 3 | — | 8 |
| | | 2016 | 9 | 3 | — | 5 |
| | Grubbenvorst | 2014 | 7 | 4 | — | 5 |
| | | 2015 | 9 | 3 | — | 8 |
| | | 2016 | 9 | 3 | — | 8 |
| Netherlands | | 2014 | 10 | 5 | — | 8 |
| | | 2015 | 7 | 4 | — | 8 |
| | Grand Mean | | 8.8 | 3.5 | 7.7 | 7.4 |

| | | Fruit characteristics | | | | |
|---|---|---|---|---|---|---|
| Location | | Size | Color | Scar | Firm-ness | Flavor |
| Michigan | Grand Junction | 7 | 7 | 7 | 7 | 6 |
| | | 8 | 6 | 8 | 7 | 7 |
| | | 7 | 9 | 7 | 8 | 6 |
| Oregon | Lowell | 9 | 7 | 9 | 8 | 6 |
| | | 6 | 6 | 7 | 6 | 7 |
| | | 9 | 4 | 7 | 8 | 6 |
| | Grubbenvorst | 7+ | 5 | 7+ | 6 | 7 |
| | | 7 | 6 | 9 | 5+ | 7 |
| | | 7 | 6 | 9 | 6 | 7 |
| Netherlands | | 6 | 6 | 6 | 6 | — |
| | | 6 | 8 | 7 | 8 | — |
| | Grand Mean | 7.2 | 7.0 | 7.5 | 7.5 | 6.6 |

Two year old plants were set at 4 × 10' spacing in 2012. Evaluations were made when the bushes were 30-50% ripe. For bush habit, 1 = sprawling, 5 = bushy and 9 = upright. For season, 1 = very early, 4-5 = mid-season and 9 = very late. The rating scale for vigor and fruit characteristics was 1-9, with 1-4 = inferior, 5-6 = acceptable, 7 = good, 8 = excellent and 9 = superior.

TABLE 2

Mean fruit ratings and ranges (parenthesis) of 'Katahdin' and 5 other cultivars at Grand Junction, Michigan in 2014, 2015 and 2016.

| Cultivar | Date First harvest | Plant habit | Winter hardiness | Plant vigor | Fruit Weight |
|---|---|---|---|---|---|
| Duke | 6/30 (6/29-7/1) | 5 (4-6) | 6.5 (6-7) | 6 (all 6s) | 6 (4-8) |
| Bluecrop | 7/4 (7/2-7/6) | 4.7 (4-5) | 6.5 (6-7) | 6.9 (6-7) | 6.5 (6-7) |
| Draper | 7/4 (6/27-7/7) | 4.7 (4-5) | 8 (7-9) | 5.5 (5-6) | 7.6 (7-9) |
| Katandin | 7/10 (7/9/-7/11) | 9 (all 9s) | 8.5 (8-9) | 7 (all 7s) | 7 (6-8) |
| Legacy | 7/14 (7/14-7/15) | 6.7 (5-7) | 6 (5-7) | 9 (all 9s) | 6 (all 6s) |

| Cultivar | Fruit Color | Picking scar | Firmness | Flavor | Yield |
|---|---|---|---|---|---|
| Duke | 6 (all 6s) | 7 (all 7s) | 8.5 (7-10) | 6 (all 6s) | 5.5 (5-6) |
| Bluecrop | 6.5 (6-7) | 7.5 (7-8) | 8.0 (7-9) | 6.5 (6-7) | 5.5 (5-6) |
| Draper | 8.5 (8-9) | 8.6 (8-9) | 8.8 (8-9) | 7.2 (7-8) | 6.5 (5-9) |
| Katandin | 6 (4-8) | 8.5 (8-9) | 8.5 (8-9) | 6.3 (6-7) | 7.4 (7-8) |
| Legacy | 6.5 (6-7) | 7.0 (all 7s) | 8.5 (8-9) | 7.8 (7-8) | 6.5 (7-8) |

Two-year-old plants were set in 2013. Fruit evaluations were made when the bushes were 30-50% ripe. The rating scale for the vigor, hardiness and fruit characteristics were 1-9, with 1-4 = inferior, 5-6 = acceptable, 7 = good, 8 = excellent and 9 = superior. For bush habit, 1 = sprawling, 5 = bushy and 9 = upright.

TABLE 3

Average fruit physical and biochemical characteristics of 'Katahdin' compared to standard cultivars in Grand Junction Michigan (2016 & 2017).

| Cultivar | Year | Weight (g) | Soluble solids | Titratable acidity | SS/TA | Firmness (g/mm) |
|---|---|---|---|---|---|---|
| Duke | 2016 | 1.5a | 11.6a | 0.59a | 19.7b | 302b |
| | 2017 | 2.1a | 12.0a | 0.81c | 14.8ab | 183b |
| Bluecrop | 2016 | 1.6a | 11.1a | 0.80bc | 13.9ab | 202a |
| | 2017 | 2.3ab | 11.8a | 0.67b | 17.6b | 163a |
| Draper | 2016 | 2.1b | 12.7c | 0.89c | 14.3ab | 334h |
| | 2017 | 2.3ab | 11.9a | 1.05d | 12.1a | 167a |
| Katandin | 2016 | 2.1b | 12.1b | 0.91c | 13.3a | 302b |
| | 2017 | 2.5b | 12.7b | 1.01d | 12.6a | 165a |
| Legacy | 2016 | 2.0b | 12.1b | 0.73b | 16.6b | 301b |
| | 2017 | 2.1a | 13.3b | 0.52a | 25.6c | 173ab |

Three, five-fruit samples were evaluated when the bushes were 30-50% ripe.

What is claimed is:

1. A new and distinct highbush blueberry plant, substantially as described and illustrated herein.

* * * * *